United States Patent [19]

Katafuchi

[11] Patent Number: 4,563,097

[45] Date of Patent: Jan. 7, 1986

[54] METHOD OF EVALUATING COOLING PERFORMANCE OF HEAT TREATMENT AGENT AND APPARATUS THEREFOR

[75] Inventor: Tadashi Katafuchi, Ichihara, Japan

[73] Assignee: Idemitsu Kosan Company Limited, Tokyo, Japan

[21] Appl. No.: 671,723

[22] Filed: Nov. 15, 1984

[30] Foreign Application Priority Data

Nov. 16, 1983 [JP] Japan ................................ 58-215560

[51] Int. Cl.⁴ ........................................... G01N 25/20
[52] U.S. Cl. ...................................... 374/43; 374/45; 374/57
[58] Field of Search ..................... 374/39, 40, 41, 43, 374/44, 45, 54, 57; 73/53; 219/497, 499, 501, 505

[56] References Cited

U.S. PATENT DOCUMENTS

| | | | |
|---|---|---|---|
| 2,587,622 | 3/1952 | Jaffe | 374/43 |
| 2,717,515 | 9/1955 | Pesante | 374/43 |
| 2,730,894 | 1/1956 | Husa | 374/43 |
| 3,013,427 | 12/1961 | Bender | 374/43 |
| 3,054,048 | 9/1962 | Bolston et al. | 374/16 |
| 3,968,677 | 7/1976 | Felton, Jr. et al. | 374/57 |
| 4,412,752 | 11/1983 | Cellitti et al. | 374/43 |

Primary Examiner—Charles Frankfort
Assistant Examiner—Thomas B. Will
Attorney, Agent, or Firm—Flynn, Thiel, Boutell & Tanis

[57] ABSTRACT

A method of evaluating the cooling performance of a heat treatment agent, wherein a sensor (1), in which the relationship between the electric resistance value and the temperature is known, is immersed in the heat treatment agent, a voltage and a current are applied to the sensor, the voltage and the current are made variable to change the temperature of the sensor, and a predetermined relationship is sought between the temperature and the dissipated heat value on the basis of the change in temperature. An apparatus for achieving the above-described method includes: a power supply section (5) for supplying the power to the sensor; a measurer (8) for measuring the voltage and the current value supplied to the sensor; operational units (12 and 13) for seeking the temperature and the dissipated heat value of the sensor from the voltage and the current value, which are obtained by this measurer; a comparator (15) for comparing the temperature of the sensor with a preset temperature and delivering the result of comparison to the power supply section; and a recorder for recording the temperature and the dissipated heat value, which are obtained by the operational units.

11 Claims, 6 Drawing Figures

METHOD OF EVALUATING COOLING PERFORMANCE OF HEAT TREATMENT AGENT AND APPARATUS THEREFOR

BACKGROUND OF THE INVENTION

1. Field of the Invention

This invention relates to a method of evaluating the cooling performance of a heat treatment agent and an apparatus therefor.

2. Description of the Prior Art

When articles to be treated such as metallic parts are hardened by use of a heat treatment agent such as a quenching oil, occurrences of hardening strains and quench irregularities depend on the cooling performance of the heat treatment agent. However, in addition thereto there are other major influences exerted by factors other than the cooling performance itself, such as a construction of a treatment tank including an oil tank and the like, positions and conditions of arrangement of the articles in the treatment tank, further, uniformity or nonuniformity of the fluidized conditions of the heat treatment agent in the treatment tank, nonuniformity in the distribution of temperature adjacent the articles due to the nonuniformity of the heat treatment agent, and the like. However, in the case of evaluating the cooling performance of a heat treatment agent in the past, only the heat treatment agent has been subjected to a sampling test for the evaluation of the cooling performance thereof, with the above-mentioned various factors being unable to be taken into consideration as according to K 2242 Method of Japanese Industrial Standard (JIS). Furthermore, there have been cases where trial quenches have been performed to judge the cooling performance from the results thus obtained. However, it has been impossible to obtain the objective and quantitative results in such cases as described above.

SUMMARY OF THE INVENTION

The present invention has as its object the provision of a method of evaluating the cooling performance of a heat treatment agent and an apparatus therefor, capable of evaluating the cooling performance of the heat treatment agent in consideration of various factors giving the influences to the actual heat treatments, such as the construction of the treatment tank, positions and conditions of arrangement of articles to be treated in the treatment tank or the fluidized conditions of the heat treatment agent in the treatment tank.

To this end, the method of evaluation according to the present invention contemplates that electric current is supplied to a sensor, wherein the relationship between the electric resistance value and the temperature is known, in a heat treatment agent to be evaluated, the power conditions, i.e. the relationship between the temperature of the sensor when the voltage and the current value are varied (namely, an electric resistance value of the sensor) and a dissipated heat value (namely, an electric energy supplied to the sensor, or an electric energy consumed by the sensor) is sought, and the cooling performance of the heat treatment agent is evaluated on the basis of this relationship.

To the above end, the apparatus for evaluation according to the present invention contemplates that the apparatus comprises:

a sensor wherein the relationship between the electric resistance value and the temperature is known;

a power supply section capable of varying a voltage and a current value, which are applied to the sensor;

a voltage-current measurer for measuring a voltage value and a current value, which are applied to the sensor;

a control section for seeking a temperature (the electric resistance value of the sensor) and a dissipated heat value (an electric energy supplied to the sensor or an electric energy consumed by the sensor) of the sensor from the voltage value and the current value thus obtained by this voltage-current measurer and comparing the temperature with a preset temperature value, thereby controlling the power supply section to raise the temperature of the sensor at a predetermined rate; and a recorder for recording the temperature and the dissipated heat value thus obtained by this control section.

DETAILED DESCRIPTION OF THE PREFERRED EMBODIMENT

Description will hereunder be given of one embodiment with reference to the drawings.

Figure 1:
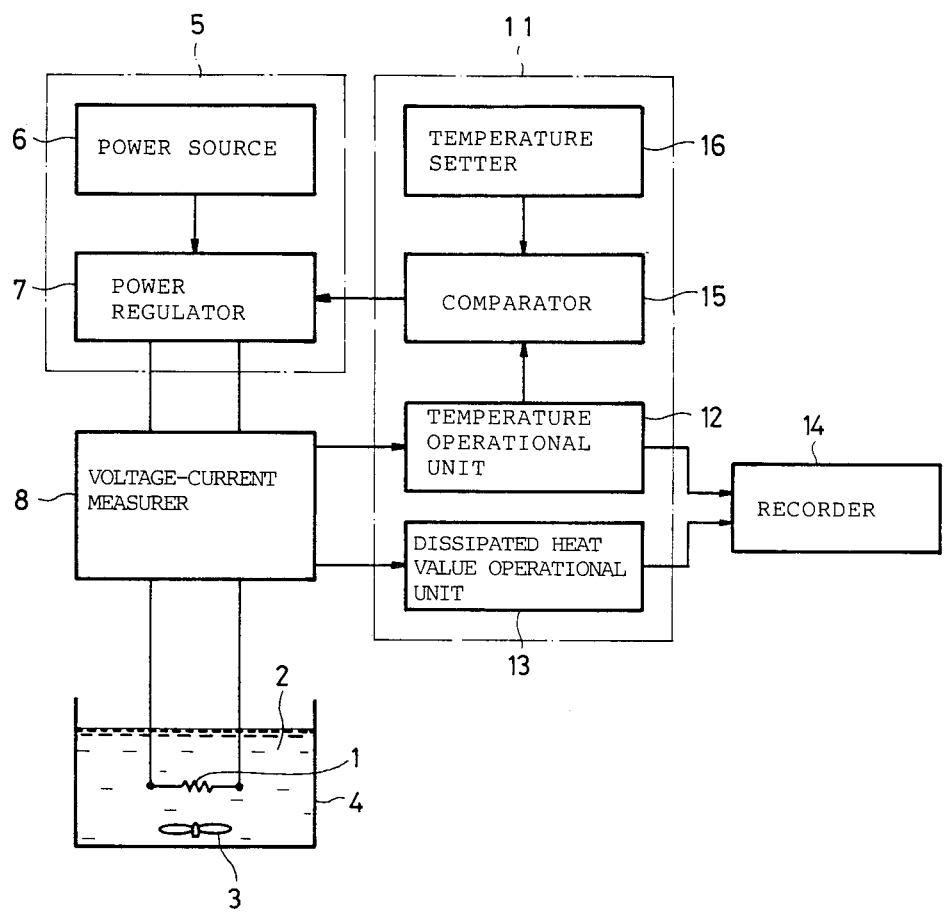
FIG. 1 is a block diagram showing the general arrangement of one embodiment of the apparatus for evaluating the cooling performance of a heat treatment agent according to the present invention.

FIG. 1 shows the general arrangement of one embodiment of the apparatus for evaluating the cooling performance of the heat treatment agent according to the present invention. Referring to the drawing, in a sensor 1, the relationship between the electric resistance value and the temperature is known, and, for example, the sensor 1 is formed of a platinum wire, an iron wire, a steel wire, a wolfram wire, a molybdenum wire, a tantalum wire, a copper wire, a nickel wire, a silver wire, a gold wire, a rhodium wire, ect. having a predetermined form. In consequence, if the electric resistance value indicated by this sensor 1 is known, then the temperature of the sensor 1 can be found.

The sensor 1 is immersed in a heat treatment agent 2 such as a quenching oil as being an object to be evaluated, and a predetermined quantity of this heat treatment agent 2 is contained in a treatment tank 4 such as an oil tank having agitating means 3.

Current is supplied to the sensor 1 from the power supply section 5. This power supply section 5 includes a power source 6 for giving predetermined values of voltage and current and a power regulator 7 for regulating an output from this power source 6 and regulating electric energy (voltage value and current value) supplied to the sensor 1.

The voltage value and current value of the sensor 1 when the power is supplied to the sensor 1 from the power supply section 5 are measured by a voltage-current measurer 8 including a voltmeter and an ammeter. The voltage value and current value of the sensor 1 which are measured here are given to a temperature operational unit 12 and a dissipated heat value operational unit 13 in the control section 11, respectively.

In the temperature operational unit 12, the voltage value given from the measurer 8 is divided by the current value to seek an electric resistance value of the sensor 1, and the temperature of the sensor 1 is calculated from the intrinsic relationship between the electric resistance value previously stored and the temperature. Furthermore, the voltage value and current value, which have been given to the dissipated heat value operational unit 13 are multiplied by each other to seek the electric energy (or the electric energy consumed by the sensor 1) supplied to the sensor 1, i.e. the dissipated heat value. The temperature and dissipated heat value of the sensor 1 obtained by these units 12 and 13 are delivered to a recorder 14 such as an X-Y recorder, and this recorder 14 records the dissipated heat value against the temperature of the sensor 1 on an X-Y Plane.

Additionally, the temperature of the sensor 1 obtained by the temperature operational unit 12 is given to a comparator 15 in the control section 11. A set temperature value preset by a temperature setter 16 is given to this comparator 15. In this comparator 15, the set temperature value is compared with the temperature of the sensor 1, the power regulator 7 is regulated on the basis of the results of the comparison, so that the sensor 1 is raised in its temperature at a predetermined rate with respect to the temperature set by the temperature setter 16.

Description will hereunder be given of action of this embodiment.

Figure 2:
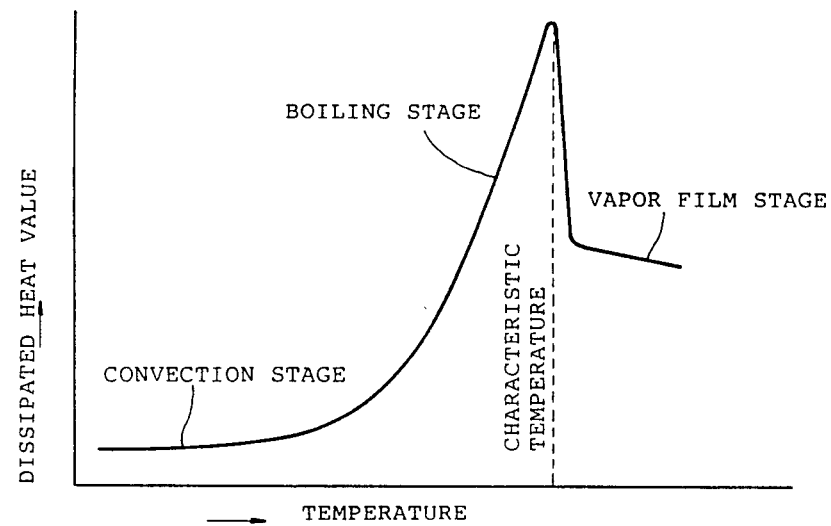
FIG. 2 is a graphic chart showing the relationship between the temperature and the dissipated heat value of the sensor when a quenching oil is evaluated by the embodiment.

Firstly, the sensor 1 is immersed in the treatment tank 4 containing the quenching oil as being the heat treatment agent 2. Upon completion of the immersion of the sensor 1, power is supplied to the sensor 1 through the power supply section 5, so that the sensor 1 is raised in its temperature at a predetermined rate with respect to the temperature value set by the temperature setter 16 in the control section 11. The voltage value and current value of the power supplied to the sensor 1 here are measured by the measurer 8, and the results of measurement are given to the temperature operational unit 12 and the dissipated heat value operational unit 13, respectively. In the temperature operational unit 12, a resistance value is sought from the voltage value and current value, and the temperature value of the sensor 1 is calculated from this resistance value on the basis of a predetermined relationship. On the other hand, in the dissipated heat value operational unit 13, electric energy (Watt) consumed by the sensor 1, i.e. a dissipated heat value of the sensor 1 is calculated from the voltage value and current value given as aforesaid. The temperature and dissipated heat value of the sensor 1, which have been calculated by the temperature operational unit 12 and the dissipated heat value operational unit 13, are recorded by the recorder 14 as shown in FIG. 2. As shown in this drawing, if the sensor 1 is risen in its temperature at a predetermined rate, then, initially, the dissipated heat value gradually increases with the increase of the temperature. However, once the gradual increase reaches a predetermined temperature, the dissipated heat value begins to increase (the rise) considerably. After the dissipated heat value abruptly increases, the dissipated heat value reaches the maximum value. Thereupon, the dissipated heat value abruptly decreases, and thereafter, decreases at a comparatively moderately reducing gradient.

Figure 3:
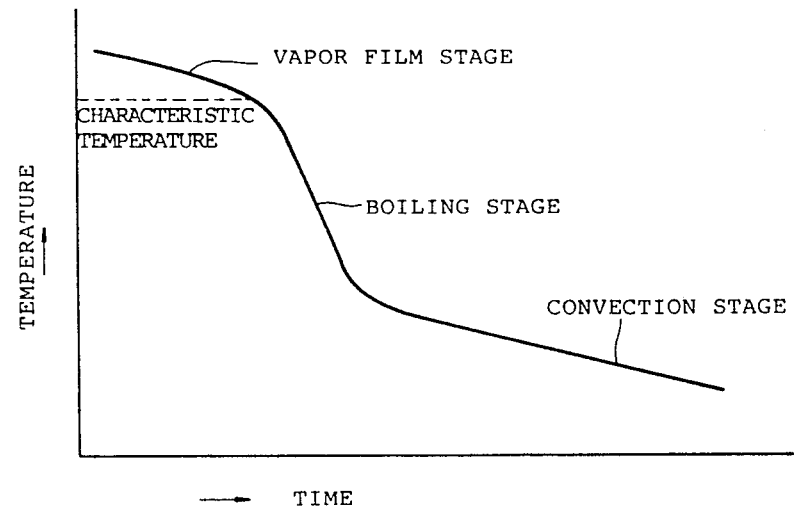
FIG. 3 is a graphic chart showing the cooling performance obtained according to the conventional method of evaluation.

Subsequently, the above-described result of evaluation is compared with the conventional result of evaluation according to the JIS regulations, which is obtained in such a manner that the articles to be treated are heated to a predetermined temperature before they are immersed in the heat treatment agent and the articles thus heated are immersed in the heat treatment agent and a change in temperature is sought as shown in FIG. 3.

FIG. 3 shows the transitional conditions in temperature of a silver piece when the silver piece, which has been heated to a predetermined temperature, is immersed in a quenching oil to be evaluated. As shown in this drawing, the temperature of the silver piece decreases moderately in a vapor film stage, is transferred to a boiling stage upon reaching the characteristic temperature (burnout point), decreases abruptly in the boiling stage, thereafter, when transferred to a convection stage, decreases moderately in the convection stage. In comparison of this with the result of evaluation of this embodiment as shown in FIG. 2, the sensor 1 in this embodiment is heated after it has been immersed in the heat treatment agent, which is contrary to the process of the conventional example, Hence, the stage, where the dissipated heat value begins to increase abruptly with the increase of temperature in this embodiment, corresponds to the convection stage of the conventional example, the stage, where the dissipated heat value increases abruptly, corresponds to the boiling stage, the stage, where, upon reaching the maximum value, the dissipated heat value decreases abruptly and thereafter decreases moderately, corresponds to the vapor film stage, and the point of the maximum value corresponds to the characteristic temperature.

The above-described embodiment can offer the following advantages.

Since the sensor 1 is disposed in the treatment tank 4 actually used to evaluate the heat treatment agent 2, the influence of the construction of the treatment tank 4, which is exerted on the cooling performance, can be also evaluated. Furthermore, the conditions and positions of arrangement of the sensor 1 in the treatment tank 4 may be changed variously, so that the influences of the conditions and positions, etc. of the articles in the treatment tank 4, which are exerted on the cooling performance can be objectively and quantitatively evaluated. Further, if the fluidized conditions of the heat treatment agent 2 in the treatment tank 4 are changed variously by the agitating means 3 for the evaluation, then the influence of the fluidized conditions and the like of the heat treatment agent 2 in the treatment tank 4 can be evaluated.

Figure 4:
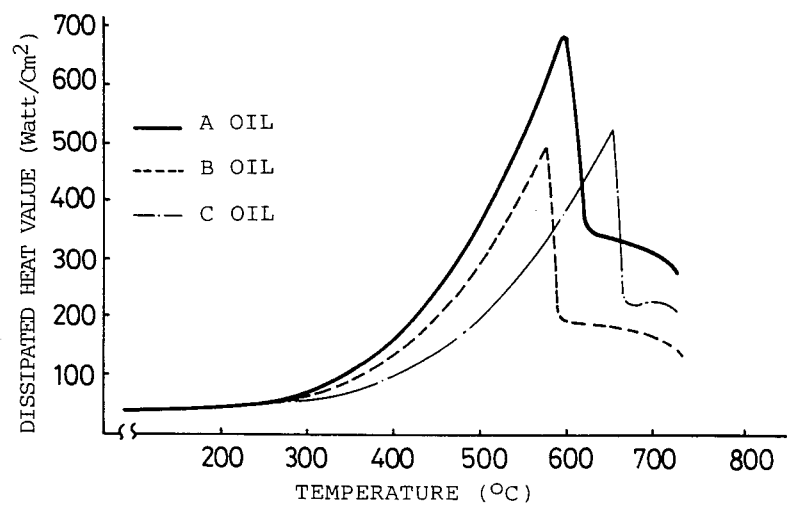
FIG. 4 is a graphic chart showing the result of evaluation of three quenching oils different in properties from one another by the embodiment.

For example, FIG. 4 shows the results of evaluation when a platinum wire having a diameter of 0.2 mm and a length of 20 mm is used as the sensor 1, and three quenching oils (oils A, B and C) different in properties from one another are evaluated. From these results of evaluation, it is found that these three quenching oils are different in properties from one another, different in cooling performance in the boiling stage from one another, and the cooling performance of the oil A in the boiling stage is very high.

Figure 5:
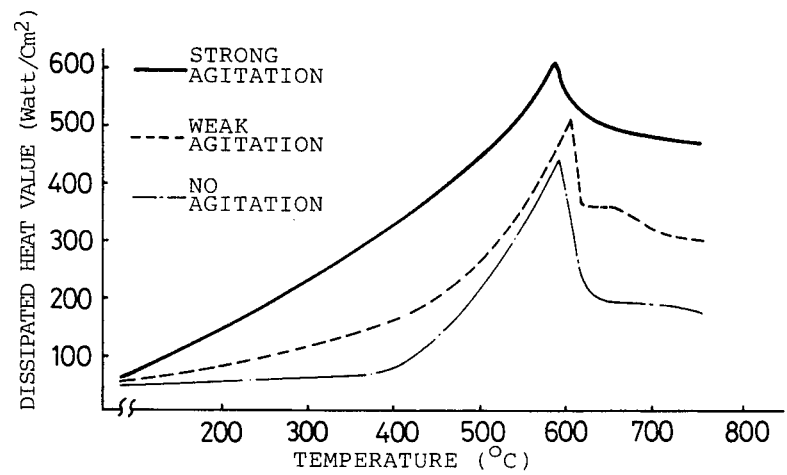
FIG. 5 is a graphic chart showing the results of evaluation by the embodiment when the agitation conditions are different from one another.

Furthermore, FIG. 5 shows the results of evaluation when the quenching oil of the same type (oil C) is used, and, when the fluidized conditions are different from each other, the respective cooling performances are evaluated. From these results of evaluation, it is found that, in the case of the quenching oil used (oil C), if the agitation is vigorously made to make the fluidization active, then, in the convection stage and at the temperature higher than the characteristic temperature, the effect of increasing the cooling capacity by the agitation is high, however, in the boiling stage, the effect of increasing the cooling capacity by the agitation is relatively low. Additionally, this coincides with the result of evaluation by use of the silver piece according to the JIS regulations, and, by obtaining several results of evaluation depending on the agitated conditions, the cooling capacities of a certain quenching oil can be further distinctly clarified from its convection stage to its boiling stage. Furthermore, from the results of evaluation as described above, it is judged that the quenching oil having a wide boiling stage area is not easily subjected to the influence of the agitation, and, even if agitation irregularities are present in the treatment tank 4, the agitation irregularities do not easily appear as cooling irregularities. Further, in general, if the quenching oil is strongly agitated, then the cooling capacity thereof can be increased. In this case, the cooling capacity in the convection stage too increases considerably, and hence, in hardening the steel, the cooling property in the transformation region of martensite is increased, whereby occurrences of quench cracks and hardening strains are possibly increased.

Figure 6:
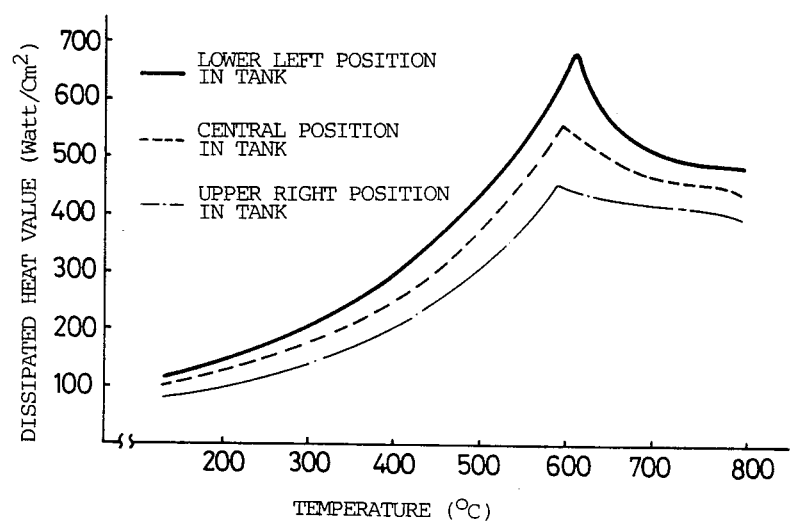
FIG. 6 is a graphic chart showing the results of evaluation by the embodiment when the sensors are in different conditions of arrangement from one another.

Furthermore, FIG. 6 shows the result of evaluation when the same quenching oil (oil B) is evaluated in the same fluidized conditions, with the positions of arrangement of the sensor 1 being different from each other. From this result of evaluation, it is found that, even if the same treatment tank 4 is used, the cooling performance are considerably different, depending upon the positions and conditions of arrangement of the articles. Moreover, the influence exerted on the cooling performance in this case can be quantitatively grasped.

Furthermore, according to this embodiment, the above-described knowledge can be obtained, so that advices can be obtained on the construction at the time of designing the treatment tank 4, advices for determining the set value of the articles in one treatment process, or advices on the positions of arrangement of the articles for conducting the effective heat treatment and so on.

Moreover, the results of evaluation can be very simply and quickly obtained, differing from the case of the evaluation method according to the JIS regulations, and the apparatus for the evaluation is simplified in construction, so that the cooling performance of the heat treatment agent can be evaluated on the site. Additionally, the apparatus for the evaluation is compact in size, so that the apparatus can be easily installed on various positions of the actual machine.

Furthermore, the temperature of the sensor 1 is controlled by the power regulator 7, whereby the sensor 1 is not melted, so that the sensor 1 can be given a long service life.

In working, the sensor 1 need not necessarily be limited to the metal wire such as the platinum wire, iron wire, copper wire, nickel wire or the like, and, semiconductors such as a thermistor, carbon coated film and the like may be used as the sensor 1. However, the sensor using the platinum wire can make the result of evaluation highly accurate. Furthermore, the heat treatment agent as being evaluated may be any heat treatment agent other than quenching oils. Additionally, the recorder 14 need not necessarily be limited to the X-Y recorder.

As has been described hereinabove, the present invention can provide the method of evaluating the cooling performance of a heat treatment agent and the apparatus therefor, capable of evaluating the cooling performance of the heat treatment agent in consideration of various factors giving the influences to the actual heat treatments, such as the construction of a treatment tank actually used, positions and conditions of arrangement of articles in the treatment tank or the fluidized conditions of the heat treatment agent in the treatment tank.

I claim:

1. A method of evaluating the cooling performance of a heat treatment agent, the steps comprising: placing a sensor in said heat treatment agent to be evaluated; supplying an electric current to said sensor for which a first relationship between its electric resistance value and its temperature is known; varying the voltage and the current values to determine a second relationship between a temperature of said sensor and a dissipated heat value, and evaluating the cooling performance of said heat treatment agent on the basis of said second relationship.

2. A method of evaluating the cooling performance of a heat treatment agent as set forth in claim 1, wherein said sensor is raised in temperature at a predetermined rate with respect to a preset temperature.

3. A method of evaluating the cooling performance of a heat treatment agent as set forth in claim 1, wherein, in varying the voltage and the current values supplied to said sensor, said heat treatment agent is agitated.

4. A method of evaluating the cooling performance of a heat treatment agent as set forth in claim 2, wherein, in varying the voltage and the current values supplied to said sensor, said heat treatment agent is agitated.

5. A method of evaluating the cooling performance of a heat treatment agent as set forth in claim 1, wherein said sensor is formed of any one material selected from materials including a platinum wire, an iron wire, a steel wire, a wolfram wire, a morybdenum wire, a tantalum wire, a copper wire, a nickel wire, a silver wire, a gold wire, and a rhodium wire.

6. A method of evaluating the cooling performance of a heat treatment agent as set forth in claim 1, wherein the temperature and the dissipated heat value are shown in a graphic chart.

7. An apparatus for evaluating the cooling performance of a heat treatment agent, comprising:
   a sensor having a known relationship between its electric resistance value and its temperature;
   a power supply section connected in circuit with said sensor and being capable of varying a voltage and a current value supplied to said sensor;
   a voltage-current measurer for measuring a voltage value and a current value supplied to said sensor;
   a control section for seeking a temperature and a dissipated heat value of said sensor from voltage values and current values obtained by said voltage-current measurer and for comparing said temperature with a preset temperature value to thereby effect a controlling of said power supply section to effect a raising of the temperature of said sensor at a predetermined rate; and a recorder for recording said temperature and said dissipated heat value thus obtained by said control section.

8. An apparatus for evaluating the cooling performance of a heat treatment agent as set forth in claim 7, wherein said control section includes: a temperature operational unit for calculating a temperature of said sensor on the basis of said voltage and said current values obtained by said measurer; and a dissipated heat value operational unit for calculating a dissipated heat value on the basis of said voltage and said current values obtained by said measurer.

9. An apparatus for evaluating the cooling performance of a heat treatment agent as set forth in claim 7, wherein said control section includes a comparator for comparing a temperature obtained by said temperature operational unit with a preset temperature.

10. An apparatus for evaluating the cooling performance of a heat treatment agent as set forth in claim 7, wherein said recorder is an X-Y recorder.

11. An apparatus for evaluating the cooling performance of a heat treatment agent as set forth in claim 7, wherein said sensor is formed of any one material selected from materials including a platinum wire, an iron wire, a steel wire, a wolfram wire, a molybdenum wire, a tantalum wire, a copper wire, a nickel wire, a silver wire, a gold wire and a rhodium wire.

* * * * *